United States Patent
Topp-Manske et al.

(10) Patent No.: US 11,697,790 B2
(45) Date of Patent: Jul. 11, 2023

(54) PROBE HOLDER AND METHOD FOR POSITIONING A PROBE

(71) Applicant: Sartorius Stedim Biotech GmbH, Goettingen (DE)

(72) Inventors: Simon Topp-Manske, Lohfelden (DE); Christian Zahnow, Goettingen (DE); Ute Husemann, Goettingen (DE); Bernward Husemann, Goettingen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 308 days.

(21) Appl. No.: 16/082,295

(22) PCT Filed: Mar. 14, 2017

(86) PCT No.: PCT/EP2017/000335
§ 371 (c)(1),
(2) Date: Sep. 5, 2018

(87) PCT Pub. No.: WO2017/211435
PCT Pub. Date: Dec. 14, 2017

(65) Prior Publication Data
US 2019/0031996 A1    Jan. 31, 2019

(30) Foreign Application Priority Data
Jun. 6, 2016    (DE) .................... 10 2016 006 916.3

(51) Int. Cl.
*C12M 1/00*    (2006.01)
*C12M 3/00*    (2006.01)
(Continued)

(52) U.S. Cl.
CPC ............ *C12M 23/48* (2013.01); *C12M 23/28* (2013.01); *C12M 23/46* (2013.01); *C12M 23/50* (2013.01); *C12M 41/00* (2013.01); *G01D 11/30* (2013.01)

(58) Field of Classification Search
CPC ...... C12M 23/28; C12M 23/46; C12M 23/48; C12M 23/50; C12M 41/00; G01D 11/30
See application file for complete search history.

(56) References Cited

U.S. PATENT DOCUMENTS

| | | | |
|---|---|---|---|
| 2005/0005717 A1 | 1/2005 | Pensis et al. | |
| 2006/0280028 A1* | 12/2006 | West ................... | B01F 7/00691 366/331 |
| 2015/0030514 A1* | 1/2015 | Feltham ................. | C12M 23/00 422/544 |

FOREIGN PATENT DOCUMENTS

| | | |
|---|---|---|
| EP | 2 829 598 | 1/2015 |
| WO | 2011/075036 | 6/2011 |

OTHER PUBLICATIONS

International Search Report dated Jun. 20, 2017.

\* cited by examiner

*Primary Examiner* — Lydia Edwards
(74) *Attorney, Agent, or Firm* — Gerald E. Hespos; Michael J. Porco (57) ABSTRACT

A probe holder (1), for positioning at least one probe (50) such that the probe (50) at least partially engages in a system (100) for biotechnological uses, comprises a holder base (10) for positioning the probe holder (1) on the system (100) for biotechnological uses and at least one probe positioning means (20), which is designed to position the at least one probe (50) such that the probe (50) extends in a probe extension direction (S; S1, S2, S3, S4). The probe positioning means (20) is positioned on the holder base (10) such (Continued)

that the position of the probe (50) is variably adjustable in a probe extension direction (S; S1, S2, S3, S4).

13 Claims, 6 Drawing Sheets (51) Int. Cl.
    *C12M 1/34*         (2006.01)
    *G01D 11/30*       (2006.01)

PROBE HOLDER AND METHOD FOR POSITIONING A PROBE

BACKGROUND

Field of the Invention

The present invention refers to a probe holder and to a method for positioning a probe on a system for biotechnological uses.

Related Art

Systems for biotechnological uses such as bioreactors and pallet tanks are used for holding, storing and/or mixing biological mediums/culture broths, such as fluids and/or solids. In particular, biological mediums may be provided in containers such as disposable containers and/or bags. The biological mediums are introduced into such a container in the system for biotechnological uses, in which they are stored, thermally treated and/or mixed. In such a system for biotechnological uses, various analyses may be conducted on the biological medium.

In particular, the manipulation of the system for biotechnological uses is usually performed in a sterile environment. The mixing of the biotechnological medium may in particular occur by means of a rotating stirring element, which is positioned outside of the container and which is driven by transmission of force from the outside of the container.

On the system for biotechnological uses one or more probes may be positioned, with which measurements on the medium may be performed inside the disposable container, such as pH measurements, etc. The probe is positioned on the system for biotechnological uses in particular in such a way that for example it penetrates through a window with its probe head through a container wall of the container, in order to physically contact the medium to be analyzed. The probe may be fixedly connected to the container.

The biological medium may be positioned within a container with flexible container walls, in particular in so called disposable containers and/or disposable bags made of plastic material. While filling the container with the medium, while stirring the medium and/or during the process, the flexible container wall may move with respect to the probe. The container wall may for example extend to a different extent. The extensions of the container wall may differ in particular by a few centimeters. This normally causes a change in orientation of the probe, the head of which penetrates into the container through a predetermined point in the container wall. Since the probe should normally be arranged with a predetermined angle and/or distance from the container, the measurement to be performed by the probe may be influenced and/or falsified. Moreover, the container and/or the probe or the probe holder may become damaged.

The object of the invention is to improve the positioning of a probe on a system for biotechnological uses, in particular in view of above said problems.

SUMMARY

A first aspect refers to a probe holder for positioning at least one probe such that the probe at least partially engages in a system for biotechnological uses. The probe holder comprises a holder base for positioning the probe holder on the system for biotechnological uses and at least one probe positioning means, which is designed to position the at least one probe such that the probe extends in a probe extension direction. The probe positioning means is positioned on the holder base such that the position of the probe is variably adjustable in a probe extension direction.

The probe holder may be adapted for positioning, holding, accommodating and/or fixing the probe on the system for biotechnological uses. In particular, the probe holder may be adapted for accommodating a plurality of probes.

The invention is described in the following with reference to a system, i.e. a system for biotechnological uses. This system may in particular be provided as a bioreactor and/or a pallet tank, i.e. a fixed container for accommodating a flexible container. The system may in particular be a single-use system for biotechnological uses, a cross-flow system, a bioreactor, a biogas-system and/or similar systems.

The system may be configured for accommodating and/or storing a disposable container, in which, in turn, a biological medium may be positioned and/or loaded, for example.

The probe is positioned and/or fixed to the system such that the probe is directed at least partially, in particular with a probe head, into the system. To this end, the probe head may physically contact the disposable container through a window of the system, for example. In particular, the probe head may also pass through a container wall of the disposable container and physically contact, for example, the biological medium, which is positioned within the disposable container. To this end a corresponding docking device for the probe may be formed on the wall of the disposable container. The probe may thus be attached or fixed at least on one side to the container wall.

The probe extension direction may be a nominal direction and may define a predetermined direction and position of the probe in the probe positioning means. The probe should preferably be positioned in this probe extension direction, when performing measurements on the medium.

The probe may essentially be oblong, and thus have a longitudinal direction. The probe may thus for example be essentially cylindrical or a parallelepiped. If the probe is appropriately positioned in the probe positioning means, the longitudinal direction of the probe may for example be positioned in and/or correspond to the probe extension direction.

In general, the probe may then be positioned in the probe extension direction when a rectilinear connection line from a probe center and/or an attachment end to the probe head, which during measurement should touch the medium, approximately coincides with the probe extension direction. The attachment end may be an end of the probe, which is directed away from the probe head. If the probe is positioned in the probe extension direction, then an action direction, a measurement direction and/or a penetration direction of the probe may essentially coincide with the probe extension direction, as the nominal direction.

A preferred probe extension direction is a direction, which is inclined by approximately 0° to 30°, in particular from approximately 5° to 20° with respect to a perpendicular to the outer surface of the system which is facing the probe. Normally, probes are positioned on a system for biotechnological uses with such a small angle with respect to the perpendicular on the outer surface facing the probe. The perpendicular is hereby referred to the outer surface of the system, through which the probe engages the system for biotechnological uses. If the probe thus engages the system through an essentially vertical outer surface, then the probe extension direction may be approximately inclined by 0° to 30° with respect to the horizontal plane.

The probe may be a sensor. This sensor may be configured for measuring one or more of the following properties of the medium:

pH value,
$CO_2$ content,
$O_2$ content,
methanol content,
glucose content,
lactate content,
% of biomass,
light diffusion,
electrical capacity, and
conductivity.

A probe may also be a spectroscope which is positioned in the probe holder.

The probe holder may in particular be configured for receiving a probe and/or for positioning on the system, which may be fixedly connected to the disposable container, at least on one side.

The probe may be positioned in the probe positioning means such that the probe extends, for example, in the predetermined probe extension direction. To this end, for example, the longitudinal direction and/or the action direction, etc., of the probe may be positioned in the probe extension direction. The probe positioning means may be configured for receiving, positioning, holding and/or fixing the probe in the probe extension direction. In particular, the probe positioning means may be, for example, a clip, into which the probe may be introduced and housed.

The holder base may be configured as a holder for the probe positioning means. The holder base may be directly attached and/or may be directly attachable to the holder base. The holder base may, for example, be positioned at and/or in proximity of a window or edge of system. To this end, on the system corresponding attachment means may be provided, such as rails, system rails, handles and/or hand rails. The holder base may for example be attached to the system by means of a form fit, a screwed connection and/or a press fit. The holder base may be at least partially fixed to the system, i.e. it may be at least partially fixed to the system, such that it essentially doesn't move anymore with this part with respect to the system.

The probe positioning means is positioned and/or attached to the holder base such that it is movable relative to the holder base (and thus in an operating position also relative to the system) in the probe extension direction. In particular, the position of the probe positioning means and thus of a probe positioned on the same may be variably adjusted in the probe extension direction. To this end, the probe positioning means is positioned on the holder base such that exactly this relative position of the probe positioning means with respect to the holder base may be controllably set in the probe extension direction. To this end, a corresponding attachment of both components of the probe holder (i.e. the probe positioning means and the holder base) is provided, which allows the adjustment of the position in at least this one direction.

The attachment of the probe positioning means to the holder base may also be provided with various adjustable degrees of freedom of motion. In particular, the adjustment of the position of the probe may be facilitated in all three directions of motion, in particular by interacting with the adjustment and/or positioning of the probe positioning means and of the holder base.

The adjustment of the position of the probe and of the probe positioning means in the probe extension direction allows to react with respect to an extension of the wall of the disposable container. The adjustment possibility in the probe extension direction is at least provided by an extension length, which corresponds to a difference between a usual minimum extension of the disposable container and a usual maximum extension of the disposable container in the probe position. The possible adjustment may also be provided over a longer stretch, such as over at least two times or three times the extension length.

Since the container wall of the disposable container usually expands or retracts essentially perpendicularly to the outer surface of the system, and the probe extension direction is usually only inclined to the perpendicular by a small angle (see above), the probe extension direction is particularly suitable for adjusting the position of the probe with respect to such an expansion.

Through this capacity of adjustment, an individual expansion may be reacted to, and the position of each individual probe may be improved and/or optimized with respect to the system. In this way both the precision of the respective measurement may be improved and damages to the disposable container or the probe may be reduced.

According to an embodiment, the probe positioning means is positioned on the holder base such that the position of the probe is automatically adjusted in the probe extension direction by exerting a force in the probe extension direction. This exertion of a force in the probe extension direction may in particular be obtained by the expanding and/or retracting container wall. Even if this expansion and/or contraction does not exactly occur in and/or against the probe extension direction, then the expansion and/or contraction movement causes a force to be exerted with at least a direction component in or against the probe extension direction. An expansion and/or contraction of the container may be enough to cause such a force to be exerted onto the probe, which is fixed to the container. This may be accomplished in that the probe positioning means is essentially positioned and/or fixed to the holder base in a "loose" manner and/or such that it is at least movable in the probe extension direction (in particular at least movable along certain stretches). The probe positioning means may thus be positioned on the holder base such that the holder base only bears the weight of the probe positioning means, without statically fixing the position and/or the orientation of the probe positioning means (and of the probe, if present), at least in the probe extension direction. A freedom of motion, at least along stretches, of the probe positioning means in spatial directions, which are perpendicular to the probe extension direction, may be hindered and/or (for example approximately completely) prevented. In addition to the freedom of motion, at least along stretches, in the probe extension direction, an at least partial freedom of rotation of the probe positioning means may be allowed.

The variable adjustment of the probe and of the probe positioning means in the probe extension direction may cause the distance of the probe with respect to the container (such as a flexible disposable and/or one-way container) with which the probe is engaged, to remain essentially constant, without variations, regardless of movements of the container wall (such as expansion, contraction). If the container wall during a process bulges outwards and/or inwards, such as due to an increasing and/or decreasing content, the probe positioning means may cause on the holder base a synchronized outwards motion of the probe held on the probe positioning means, in particular of the same extent of the container's bulge. The distance of the probe from the container wall thus remains approximately the same and/or constant. The same essentially holds for a preferred inclination angle of the probe. In this way, a mechanical stress on the container wall is reduced, such as in the case of a conventional, rigidly fixed probe, which does not follow the motion of the flexible container wall. The synchronization of the motion of the probe positioning means with the probe and the motion of the container wall may also cause the immersion depth of the probe head and/or of a probe tip into the inner space of the container to remain essentially constant.

According to an embodiment, the probe positioning means is configured to essentially completely bear the weight of the probe, when the probe is positioned in the probe extension direction, i.e. for example when the probe is housed within the probe positioning means. To this end, the probe positioning means carries the probe essentially completely, however without defining and/or statically fixing the position of the probe in the probe extension direction. The probe positioning means thus is completely carrying the probe and may completely house the movably supported probe. To this end, the probe positioning means may mechanically contact, hold and/or support the probe at at least two holding points, which are separated in the probe extension direction. In particular, the probe positioning means may be configured in such a way that it supports the weight of the probe itself in an operating position, in which the probe head engages in the disposable container, still to at least approximately 80% of the probe weight, preferably to at least approximately 90% and most preferably to at least approximately 99% of the probe weight. In this way both a simplification of the installation and/or start-up of the system and a reduction of the loads while transitioning from the disposable container to the probe may be accomplished.

According to an embodiment, the probe positioning means is configured such that it houses the probe in such a way that at least a head of the probe is freely directed out of the probe positioning means and in the probe extension direction towards the system. The probe positioning means holds the probe just at holding points and/or holding areas, which are distanced from the head. The probe head thus remains "free floating" as long as it is not introduced into the disposable bag. The probe positioning means is provided such as to be positioned at least partially separated from the system in the probe extension direction, so that it may position and/or house the probe in this separated position with the probe head ahead in abutment and into the disposable bag.

According to an embodiment, the probe positioning means is configured such that it houses the probe with a form fit and/or force fit. In particular, the probe positioning means may be provided for example as a clip, into which the probe may be clamped. In particular the probe may be blocked with the probe positioning means against a blocking resistance. In this way an easy to be actuated attachment of the probe to the system may be provided.

According to an embodiment, the holder base has an attachment bar, onto which the probe positioning means is positioned in such a way that the position of the probe may be variably adjusted in the probe extension direction. In particular, the attachment bar may be at least partially provided with a round or angular cross section. The probe positioning means is attached to the attachment bar, for example, by clamping, screwing and/or by means of a form fit. To this end, for example, through an adjustment of the holder base, the position of the attachment bar may be adjusted and/or set. In this way, the position of the probe positioning means and thus of the probe may be adjusted in an additional direction, which may be different from the probe extension direction.

In a development of this embodiment, the probe positioning means may be displaced in the probe extension direction, in order to position the attachment bar on the attachment bar in a rotational way and/or in a displaceable way along the attachment bar. The displacement may be allowed for example by means of a form fit, a force fit and/or a guiding rail.

In addition to the displacing in the probe positioning means, the probe positioning means may also be rotated around the attachment bar, thus enabling a further adjustment of the relative position of the probe with respect to the system. The attachment bar thus allows a particularly easy adjustment and/or setting of the position of the probe in at least two grades of freedom, i.e. by displacement in the probe extension direction and by rotation around the attachment bar. As an alternative or in addition, the probe positioning means may also be displaced along a bar extension direction of the attachment bar, whereby a further possible adjustment is provided.

In a development of the embodiment with the attachment bar, the attachment bar is positioned, at least in an attachment region, on which the probe positioning means is arranged, essentially perpendicularly to the probe extension direction. The attachment region is herein the region of the attachment bar, onto which the probe positioning means is positioned. The attachment bar may be at least partially formed and positioned essentially in parallel to the outer surface of the system, close to which the attachment bar is positioned. The attachment bar may in particular be curved, wherein the bending of the attachment bar corresponds and/or follows the curvature of a curved, for example convex outer surface of the system. If the attachment bar is positioned at and/or close to an essentially vertical outer surface of the system, then the attachment bar may be positioned in an essentially horizontal direction.

In a development of the embodiment with the attachment bar, the probe positioning means has an attachment means, through which it may be attached to the attachment bar by means of a form fit and/or a force fit. Such an attachment means, i.e. for example an attachment clip, may be adjusted in a particularly easy and/or comfortable way by an operator. The position of the probe positioning means and thus of the probe may be adjusted and/or set with respect to the holder base and thus to the system.

In a development of the embodiment with the attachment bar, a plurality of probe positioning means is positioned on the attachment bar for positioning at least one respective probe, such that the position of the respective probe may be variably adjusted in its respective probe extension direction. In this way, the number of probe positioning means and thus of probes may be increased, which are positioned on the system. The probe positioning means may be essentially constructed in the same way, thus in particular constructively corresponding to the above described probe positioning means. In particular, the attachment bar may be configured for attachment of two, four or more of the probe positioning means, wherein a probe positioning means and/or a probe may not necessarily be actually positioned at all the positions provided for these probe positioning means. In particular, for each probe positioning means a corresponding probe extension direction may be provided. These many probe extension directions may slightly differ from one another, i.e. for example they may differ by a few degrees from one another. The probe extension directions may in particular follow the outer surface facing the respective probe, so that the respective probe extension directions may be positioned with the same inclination with respect to the perpendicular to the incident surface of the system associated to the same. The use of an attachment bar for attaching a plurality of probe positioning means and thus of a plurality of probes is thus particularly efficient and requires a few components.

In a development of the embodiment with the attachment bar, the holder base has at least two attachment bars, to which at least a respective probe positioning means for arranging at least one respective probe is positioned such that a position of the respective probe may be variably adjusted in its respective probe extension direction. The at least two attachment bars may be positioned, for example essentially in parallel to an outer surface of the system, in a mutually offset way, for example vertically superimposed. The at least two attachment bars may be essentially parallel to each other. In this way the number of probe positioning means and thus of probes which may be positioned on the system may be increased. For the plurality of probe positioning means the same holds as for the previously described embodiment. The probe positioning means may essentially be constructed in the same way, i.e. in particular in the same way as the previously described probe positioning means. In particular, not at all sites provided for the probe positioning means must a probe positioning means and/or a probe be actually positioned. For each probe positioning means a separate probe extension direction may be provided. This plurality of probe extension directions may be slightly different, i.e. for example by a few degrees. The probe extension directions may in particular follow the outer surface of the system, so that the respective probe extension directions may be positioned with the same inclination with respect to the perpendicular on their respectively associated incident surface of the system. As described in the context of the previous development, a plurality of respective probe positioning means may be positioned on the different attachment bars.

According to an embodiment, the holder base is positioned on the system for biotechnological uses, such that a position of the probe positioning means may be variably adjusted in a direction of the outer surface of the system for biotechnological uses, wherein the direction of the outer surface is approximately parallel to an outer surface of the system for biotechnological uses and forms an angle of at least 45° with respect to the probe extension direction. In particular, the direction of the outer surface may be provided as an extension direction of the surface of the system facing the probe, such as an essentially vertical direction. The direction of the outer surface may be positioned at an angle of approximately 45° to 90° with respect to the probe extension direction, preferably of between approximately 65° and 85° to the probe extension direction. Thus, the holder base may for example be provided in at least two parts, wherein a first component of the holder base is attached to the system, while the probe positioning means is positioned on the second component of the holder base. Both components of the holder base may be moved in the direction of the outer surface relative to one another. This form of the holder base thus allows the adjustment of the position of the probe relative to the system by a further degree of freedom.

In a development of this embodiment, the holder base has a groove and a tongue engaging the groove, wherein the groove and the tongue are approximately parallel to each other and extend in parallel to the direction of the outer surface facing the probe. A connection between two components of the holder base by means of a tongue and groove connection allows for a simple way to implement the previously described adjusting capacity. The tongue may additionally be screwed tight in the groove.

A further aspect refers to a system for biotechnological uses for receiving a disposable container having a probe holder according to the first aspect, wherein the at least one probe is positioned in the probe holder in the probe extension direction. In particular, a plurality of such probe holders may be positioned on the system for biotechnological uses, and/or a plurality of probes may be positioned in the one or more probe holders.

In one example of the system for biotechnological uses, the disposable container is positioned within the system for biotechnological uses. A probe head engages through a container wall of the disposable container into the inner space of the disposable container.

The probe may in particular be fixedly connected with its probe head to the container wall of the disposable container. The probe holder may support the weight of the probe and thus fix and/or define the orientation of the probe in at least one vertical spatial direction. The precise orientation of the probe in the probe extension direction may in particular be determined by the expanding and/or retracting disposable container, to the container wall of which the probe is attached.

A further aspect refers to a method for positioning at least one probe such that the probe engages at least partially into system for biotechnological uses, having the steps of:
  providing a holder base for positioning a probe holder on the system for biotechnological uses;
  positioning a probe in a probe positioning means, which is positioned on the holder base, such that the probe extends in a probe extension direction; and
  variably adjusting a position of the probe in the probe extension direction.

The method may in particular be performed by means of a probe holder according to the first aspect and/or on a system for biotechnological uses according to the second aspect. Thus, all statements made in relation to these two aspects also refer to the method according to the third aspect. The variable adjustment of the position of the probe in the probe extension direction may be causes in particular by a container wall, to which the probe is attached.

The invention will be explained in the following by means of exemplary embodiments, which are shown in the figures. Individual characteristics which are shown in the figures may be combined with other examples in order to form other embodiments. The same reference numbers refer to the same or similar characteristics of the examples shown. In particular:

DETAILED DESCRIPTION

Figure 1A:
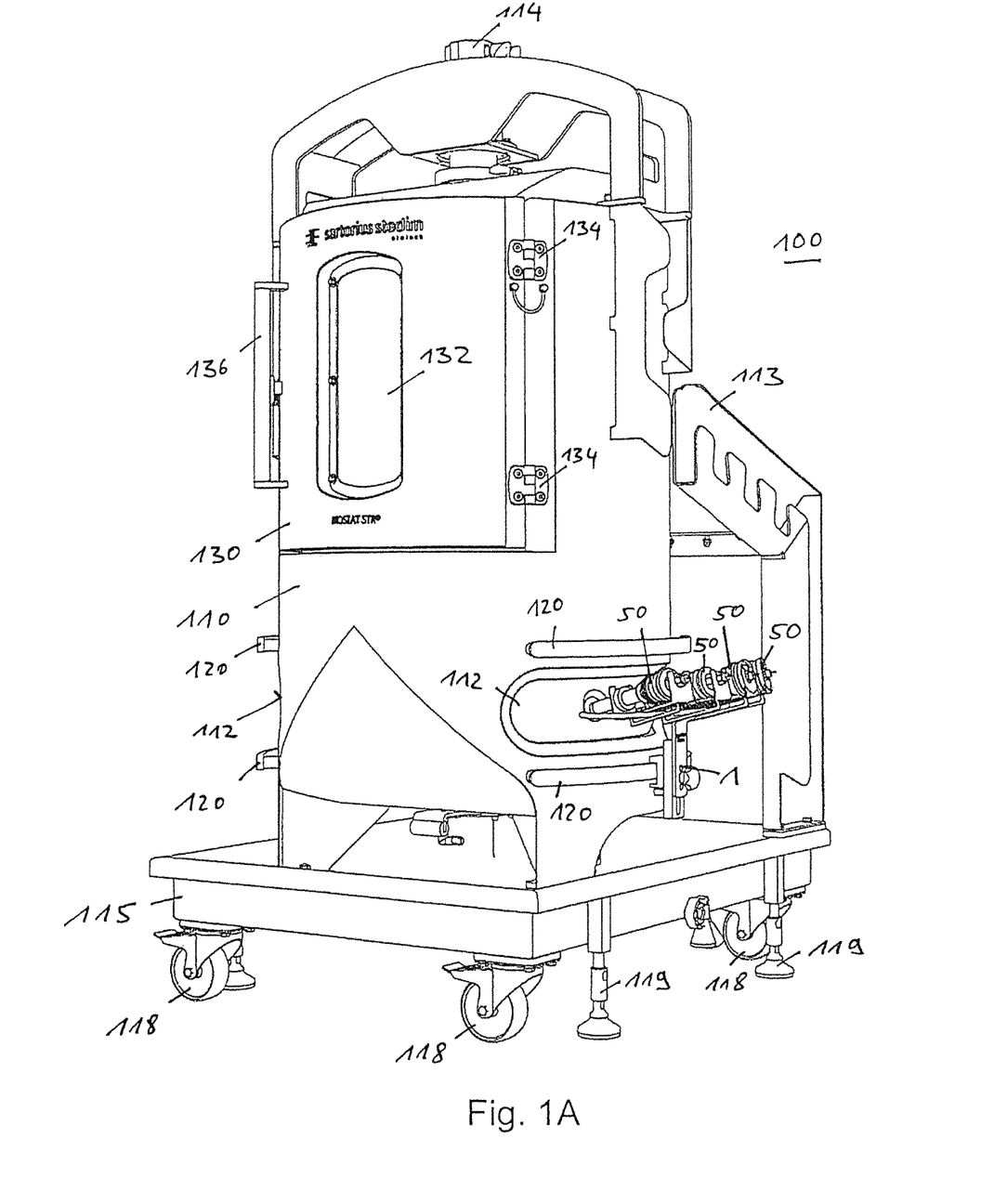
FIG. 1A shows a perspective view of the system for biotechnological uses for receiving a disposable container.

FIG. 1A shows a perspective view of a system 100 for receiving a disposable container. The system 100 is designed as a system for biotechnological uses and has a receiving container 110, which in particular essentially has the shape of a (in particular substantially vertically arranged) cylinder, i.e. whose cylinder axis is disposed substantially vertically. The receiving container 110 has a container interior, in which a disposable container can be at least partially introduced, which may include, for example, a biological medium. The biological medium in the disposable container is stored in the interior of the receiving container 110 over a predeterminable period of time and/or in a sterile manner. While the disposable container with the biological medium is within the receiving container 110, different reactions may occur with or on the biological medium. Thus, the system 100 may also be designed as a bioreactor and/or a pallet tank.

The system 100 may in particular be a single-use system for biotechnological uses, a cross-flow system, a filtration system, a bioreactor tank, a biogas system, a mixer or mixing system, a shaker, a freezing and thawing tank, a device for the treatment of fluids and/or similar systems. The system for biotechnological uses (such as a bioreactor) may in particular comprise containers in which specially grown microorganisms and/or cells are cultivated under optimally controlled (in particular sterile) conditions in a nutrient medium, in order to harvest either the cells themselves, parts of them and/or one of their metabolic products. To this end, one or more feeds and/or discharge lines are required for the respective individual products or substances. Specifically, solid (biomass), liquid (nutrient medium) and/or gaseous (e.g., air, oxygen, carbon dioxide, nitrogen) phases may be processed in the bioreactors. In order to ensure optimum conditions, one or more (different) parameters in the interior of the system are usually measured or monitored by means of sensors and/or probes 50, which protrude into the inner space of the system. Possible parameters to be measured are, for example, the pH, the O2 value and the temperature of the medium contained within the system. If parameters deviate from predefined optimal values, the deviations can be corrected by means of suitable measures. Systems can be designed for multiple use or as a disposable system or bioreactor. The system 100 may be provided to the user as a sterile unit.

In order to observe and/or monitor the biological medium, one or more viewing windows are formed in the side walls, through which the interior of the receiving container 110 can be viewed from the outside through the receiving container wall in order to observe the biological medium, and/or to extend at least partially one or more probes through the receiving container 110 into the disposable container or examine and/or control its contents. For this purpose, the system 100 has one or more (for example two) bottom windows 112 and/or a door window 132 in a lower region (for example in the lower third). The bottom windows 112 are in particular designed essentially in the form of an elongated oval whose long oval axis is aligned substantially horizontally along the (in particular curved) cylindrical outer wall of the receiving container 110. The door window 132 is formed substantially in the shape of an elongated rectangle with its longer sides substantially vertically aligned and formed in the center of a single-leaf door 130 in the container wall of the receiving container 110.

The single-leaf door 130 is formed substantially in the upper region (such as in the upper two-thirds) of the receiving container 110, while the lower region (such as the lower third) of the receiving container 110 is formed substantially in the form of a rigid bottom shell, which is not openable in itself. The single-leaf door 130 may be rotated about door hinges 134 and thus be openable. In particular, a door knob 136 may be provided for opening the single-leaf door 130. If the single-leaf door 130 is opened, a door opening is formed in the receiving container 110 at a lateral position, by which access to the interior of the receiving container 110 is permitted. Through the door opening, for example, the disposable container can be introduced into the interior of the receiving container 110 from a lateral, sideways direction, i.e., essentially in a horizontal direction of movement.

The system 100 is slidably or rollably mounted on rollers 118, on which the system may be pushed through a room. In addition to the rollers 118, the system 100 may be provided at the lower end with fixing feet 119, which are used for fastening and proper alignment of the system 100 on an uneven floor.

The receiving container 110 may open upwards. Instead of an upper cylinder lid, the receiving container 110 is provided with a stirring opening. A stirring device 114 is formed above the upwardly opened receiving container 110, and a stirring rod may be connected to the disposable container through the stirring opening in such a way that the inner space of the disposable container may be mixed. The stirring rod may be positioned within the disposable container and may be connected through a coupling or clutch to the stirring device. The stirring device 114 is centrally formed above the receiving container 110 and is supported by a supporting bridge, which rests on an upper edge of the receiving container 110 on opposite side walls of the receiving container 110.

Cable guides 113 may be positioned laterally on the system 100, and connection cables for the stirring device 114 and/or sensors/probes may pass through the guides.

A biological medium may be loaded into the inner space of the receiving container 110 and also within the disposable container. The disposable container may be emptied after use for example through a discharging port which is positioned beneath the system 100 and then completely disposed of. By using the disposable container, the cleaning of the system 100 may be omitted or considerably accelerated.

A collection container 115 beneath the receiving container 110 is used as a capture element, if for example biological medium exits the system 100 through a leak in the disposable bag.

System rails 120 are positioned near and/or adjacent to the bottom windows 112. The system rails 120 are positioned such that they are essentially parallel to a longitudinal direction of the respective bottom window 112 along an outer surface of the system 100. In the embodiment shown, the system 100 is provided with a respective system rail 120 both vertically above and vertically beneath the bottom window 112, wherein the system rail follows the outer curvature of the receiving container 110 and is respectively positioned in an essentially horizontal plane.

A probe holder 1 is positioned at one of the system rails 120, in the exemplary embodiment at one system rail 120 positioned beneath the bottom window 112. The probe holder 1 holds a plurality of probes 50, which are positioned in such a way that they are directed through the bottom window 112. The probe holder 1 is configured to position and direct each of the probes 50 in a supporting way in a respective corresponding nominal position.

Figure 1B:
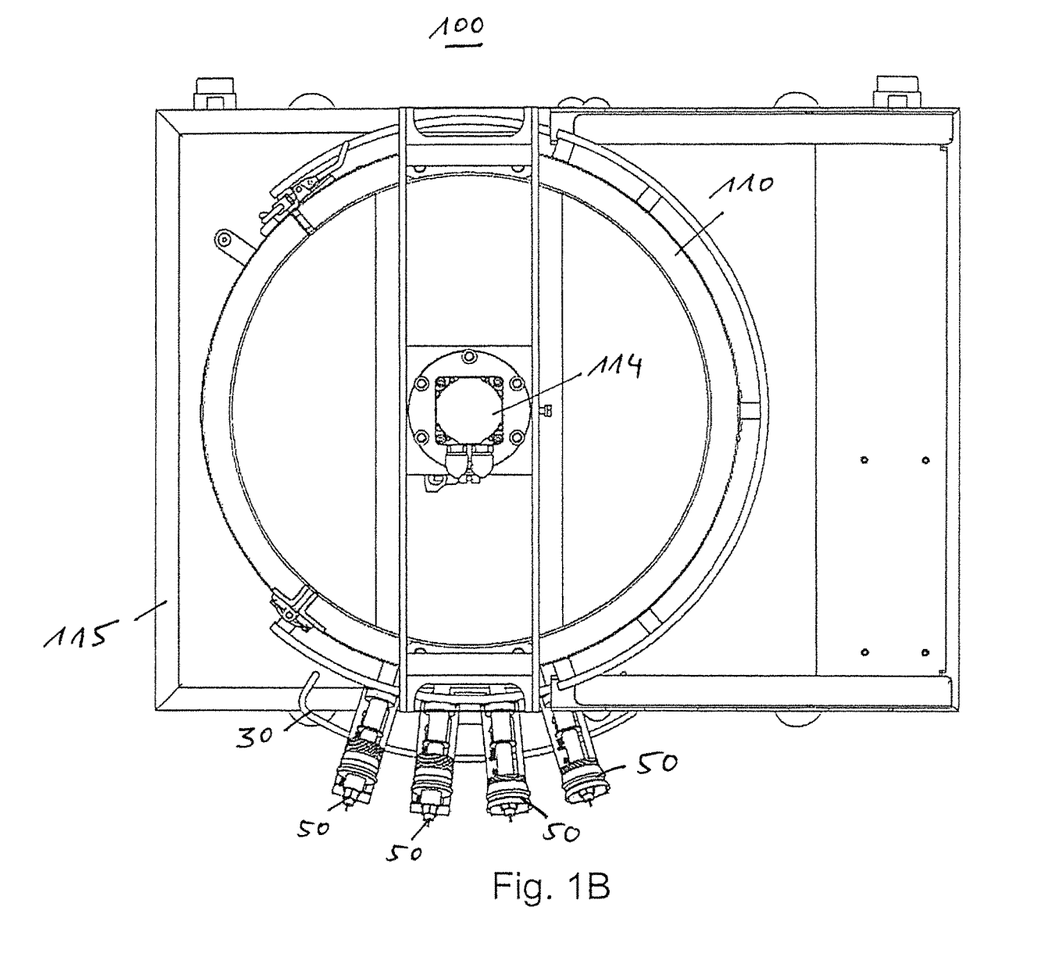
FIG. 1B shows a plan view of the system of FIG. 1A for receiving a disposable container.

FIG. 1B shows a plan view of the system 100 shown in FIG. 1A for receiving a disposable container. The probe holder 1 is configured for receiving four probes 50. Each of the probes 50 is in particular oriented in such a way that a probe head of each probe 50 (in the plan view shown in figure) is approximately directed towards the center of the receiving container 110. To this end, the center of the receiving container 110 is placed on a vertical cylinder axis of the receiving container 110.

The four probes 50 are positioned on an attachment bar 30 of the probe holder 1 and are each separated by an equal distance from one another. The attachment bar 30 has a bend and this bend follows the convex outer curvature of the receiving container 110 of system 100, so that the attachment bar 30 is essentially partially parallel to the outer surface of the receiving container 110. As shown in FIG. 1A too, the attachment bar 30 is essentially positioned in a horizontal plane. The attachment bar 30 may be part of a holding base 10, which is described in further detail in the following.

Figure 2A:
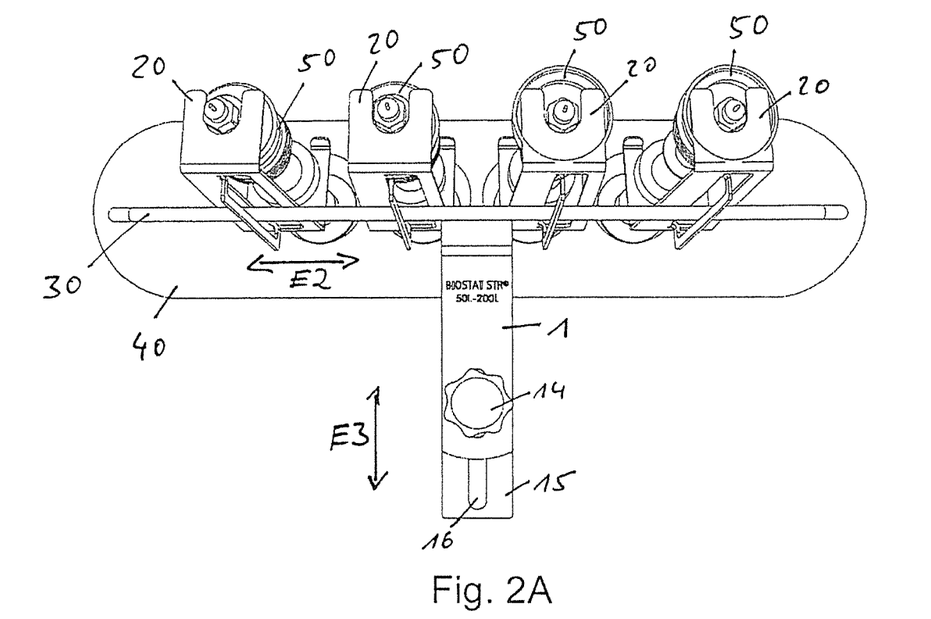
FIG. 2A shows a perspective view of a probe holder for probes, which partially engage in a disposable container.
Figure 2B:
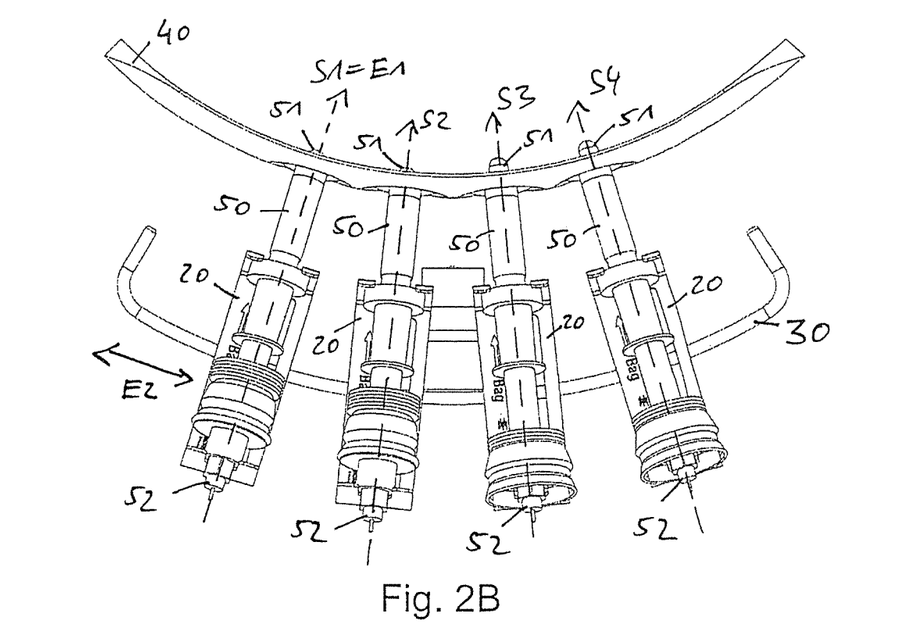
FIG. 2B shows a plan view of the probe holder shown in FIG. 2A for the probes, which partially engage in a disposable container.

FIGS. 2A and 2B show a perspective view and a plan view of the probe holder 1 for the one or more probes 50, which engage, at least partially (in particular through the bottom window 112) in a disposable container. In both figures a part of a container wall 40 of the disposable container is also shown, which may in particular be accessed through the bottom window 112 from the outside. The container wall 40 may be flexible, such as of plastic material. Thus, the position of the container wall 40 is not rigidly fixed but may vary with time. In particular the container wall 40 may expand, for example, when filling the container with the medium or after a long period of time.

The probes 50 are positioned in a nominal position, in which they are supported by the probe holder 1. In this nominal position, a respective probe head 51 of each probe 50 is positioned in such a way that it engages and/or protrudes through the bottom window 112 and through the container wall 40 at least partially in the inner space of the disposable container, wherein in particular sterility is ensured. Each of the probe heads 51 are in particular in direct physical contact with the biological medium, for example, which is loaded inside the disposable container. The probe heads 51 may in particular perform one-time or repeated measurements, or measurements over a long period of time and/or analyses on the medium, in particular in order to measure the pH of the medium, and/or a certain concentration in the medium, in order to measure the light transparency, to determine the biomass, etc.

One or more probes 50 may also be composed of a spectroscope. Each probe 50 may be configured for measuring and/or determining another measurement value. The probes 50 may thus be different from one another. The probes 50 may at least partially be single-use sensors, and/or at least partially reusable sensors.

The shape of each of the probes 50 is essentially oblong and extends from an attachment end 52, which is provided on an end of the respective probe 50 which is facing away from the probe head 51, to a respective probe head 51. Each of the probes 50 may be positioned, attached and/or housed in a respective probe positioning means 20 in a probe attachment region, which may be adjacent and/or proximate to the attachment end 52.

The probe holder 1 has one or more probe positioning means 20, in particular a number of probe positioning means 20 corresponding to the number of probes 50 it can hold and/or house, in the example shown four probe positioning means 20. The probe positioning means 20 are described and shown in further detail in the following with reference to FIGS. 5A and 5B.

In an operating position each of the probes 50 is positioned in its nominal position such that it is directed and/or aligned in its respective probe extension direction S1 to S4. This means for each probe 50 that a straight connection from its attachment end 52 to its probe head 51 essentially coincides with the probe extension direction S1 to S4 associated thereto. In other words, the longitudinal axes of the probes 50 may be aligned to the respective probe extension direction S1, S2, S3 and/or S4.

Each of the probe extension directions S1 to S4 may be directed towards the interior of the receiving container 110, in particular towards a center and/or a vertical cylinder axis, for example, of the receiving container 110.

In the plan view of FIG. 2B, which shows the probe holder 1 vertically from above, the probe extension directions S1 to S4 are positioned in such a way that they penetrate the container wall 40 along a respective approximate perpendicular direction.

Figure 3A:
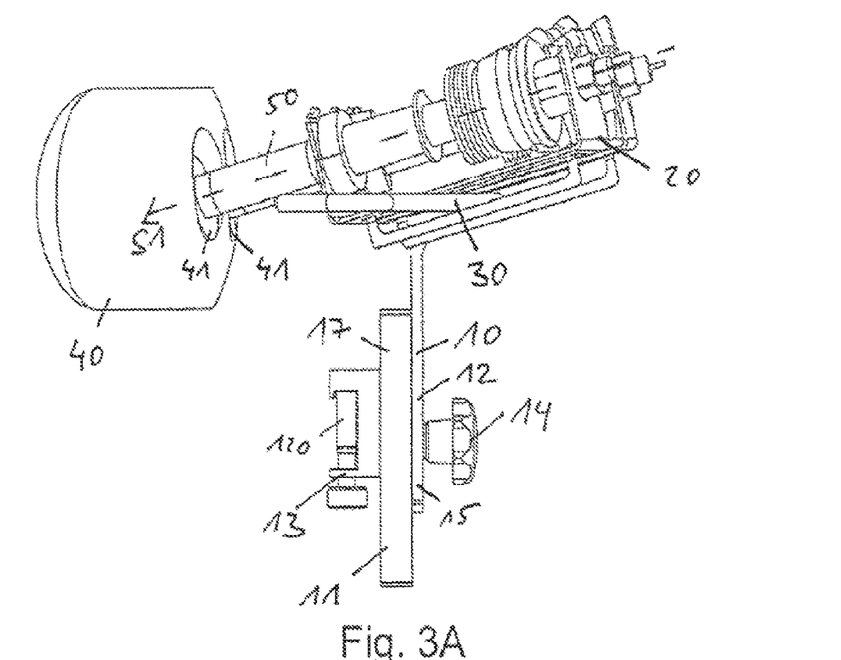
FIG. 3A shows a side view of the probe holder shown in FIG. 2A, for probes which partially engage in a disposable container.
Figure 3B:
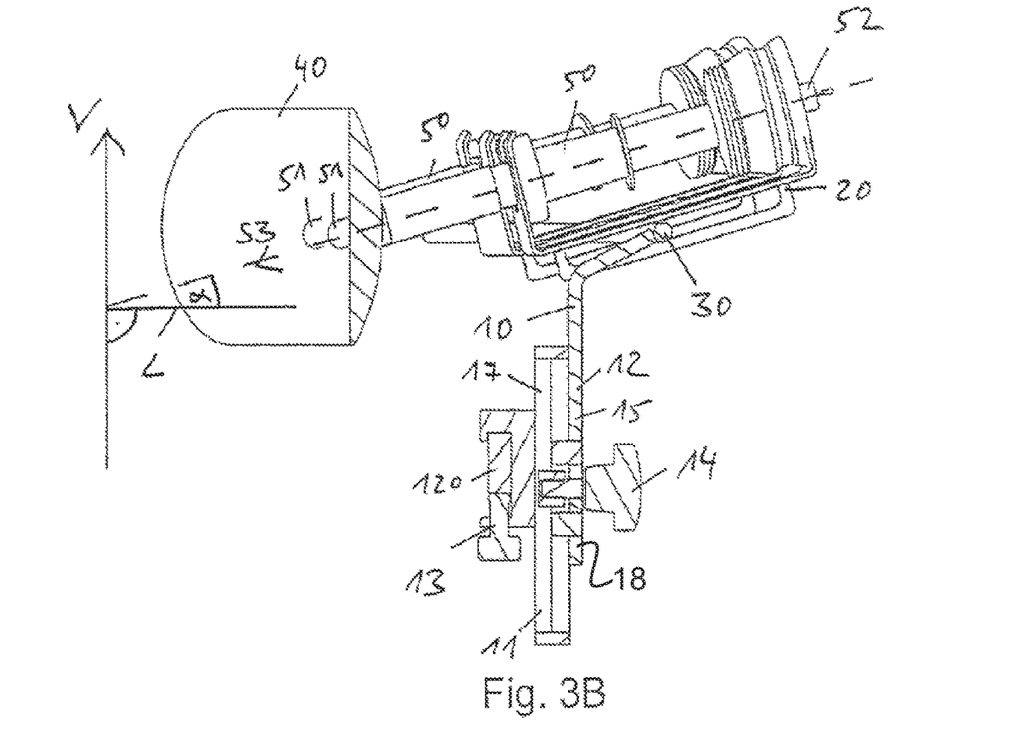
FIG. 3B shows a side sectional view of the probe holder shown in FIG. 2A for probes which partially engage in a disposable container.

FIGS. 3A and 3B show the probe holder 1 in a side view and in a lateral sectional view.

From this side view of the probe holder 1 in a substantially horizontal direction, it is shown that the probe extension directions S1 to S4 are arranged so as not to perpendicularly pierce the container wall 40, respectively. In FIG. 3B, by way of example, the third probe extension direction S3 is shown, which intersects the container wall 40 at approximately an inclination angle $\alpha$ to the perpendicular L to the container wall 40. This inclination angle $\alpha$ can be from about 10° to about 20°, for example, and may be dependent from the probe type of the corresponding probe 50. In general, due to the operation and construction of the probes 50, it is common practice to orient them at a certain angle of inclination a to the perpendicular to the outer surface of the disposable container facing the probe 50.

In the embodiment shown, the portion of the container wall 40 pierced by the probe head 51 is substantially parallel to a vertical V. Therefore, the perpendicular L to this portion of the container wall 40 is approximately parallel to the horizontal.

Docking devices 41 may be provided on the container wall 40, which are designed for docking and insertion of the probe heads 51. The docking device 41 forms a sensor port for the probe 50, which can be attached and/or fixed with its probe head 51 to the container wall 40 of the disposable container. In particular, a sterile connection between the probe head and the interior of the disposable container can thus be produced. In this case, the probe 50 can be fixedly attached to the disposable container, wherein it is supported by the probe holder 1.

In order to arrange and align the probes 50 in their respective probe extension direction S1 to S4, the probe holder 1 has the mounting base 10, which is attached to the system rail 120 of system 100, as well as the probe positioning means 20.

Figure 4A:
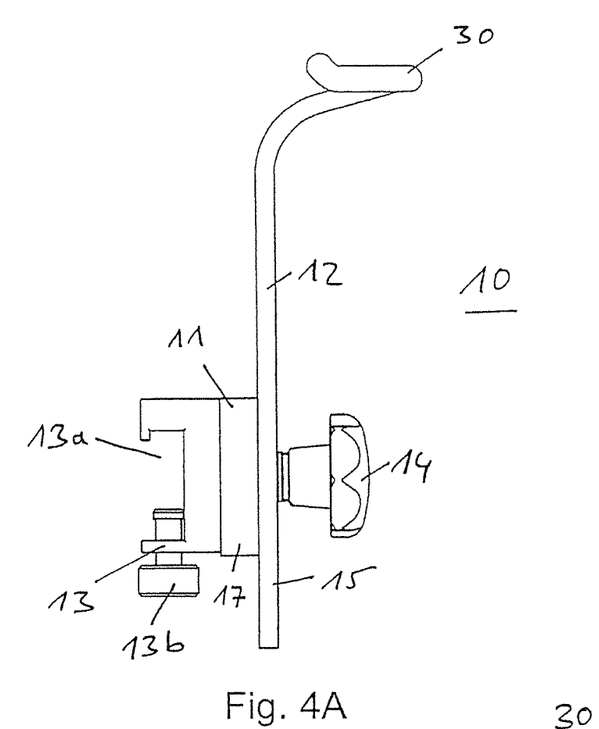
FIG. 4A shows a side view of a holder base of a probe holder.

FIG. 4A shows a side view from a substantially horizontal direction on the holding base 10 of the probe holder 1. The holding base 10 is in particular formed substantially in two parts. A first component 11 of the holding base 10 is a system-fixed component and may be fixed or stationary with respect to the system. A second component 12 of the holding base 10 is a movable component, in particular a component which may be moved with respect to the system 100.

The first component 11, which is fixed to the system, particularly comprises a positioning means 13 for positioning the probe holder 1 on the system 100. The positioning means 13 may be configured for attaching the probe holder 1 to one of the system rails 120. The positioning means 13 may for example be a recess 13a for applying the positioning means 13 on or at the system rail 120 and a screwing means 13b (as a particular releasable fixing means). The screwing means 13 may be provided with an end, which may be screwed into the recess 13, through which the probe holder 1 may be attached (in particular releasably) to the system rail 120, which is positioned within the recess 13a.

The first system-fixed component 11 may also comprise a block 17, which is rigidly connected to the positioning means 13 and thus to the system 100. An adjustment wheel 14 may be screwed into the block 17. A rail 15 of the second movable component 12 is positioned and firmly screwed between the adjustment wheel 14 and the block 17.

Figure 4B:
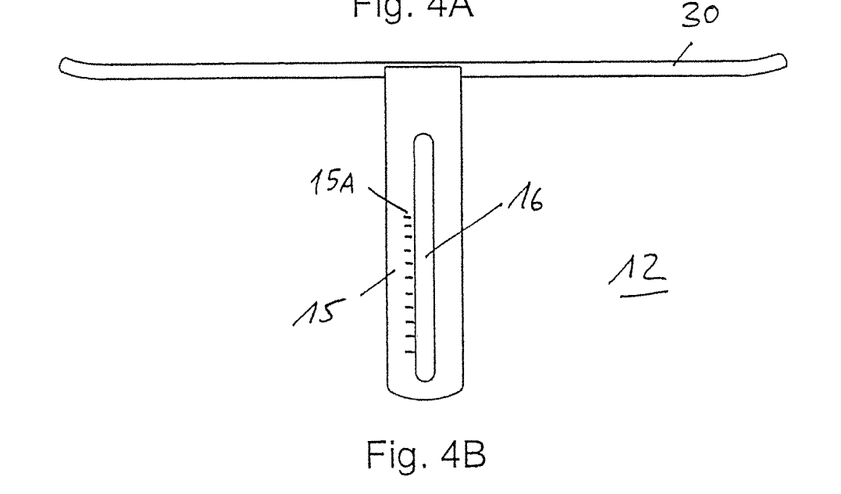
FIG. 4B shows a front view of a second movable component of the holder base of a probe holder.

FIG. 4B shows a front view of the second movable component 12 of the holder base 10 of the probe holder 1. The second movable component 12 has a rail 15, in which a groove or slot 16 is formed. The attachment bar 30 is formed at an upper end of rail 15, for example. On or at the rail 15 a scale or adjustment aid 15A may be provided, in order to more easily set the position of the movable component 12. A scale and/or adjustment aid of an alternate embodiment may also be positioned on other components of the probe holder 1 such as on the probe positioning means 20.

The groove 16 is approximately straight and extends along a longitudinal direction of the rail 15. In the example shown, the groove 16 is positioned, as the rail 15, in an essentially vertical direction. In general, the groove 16 and the rail 15 may be essentially parallel to an adjacent outer surface of the receiving container 110, in particular parallel to the non-curved extension direction of the nearby outer surface of the receiving container 110.

In an operating position, the adjustment wheel 14 and/or a screw of the adjustment wheel 14 engages in the groove 16 (see FIGS. 4A and 2A). By actuating the adjustment wheel 14, the rail 15 may be fixedly screwed to the first stationary component 11 of the holding base 10 or it may be unscrewed therefrom. In the unscrewed condition, the second movable component 12 may be displaced and/or moved with respect to the first stationary component 11. In this way, the position of the second movable component 12 may be set with respect to the system 100 and in particular with respect to docking device 41 positioned in the bottom window 112 of the disposable container.

A scale may be provided near the groove 16 on the rail 15, and the scale may allow the setting of the position of the second movable component 12 with respect to the first component 11, which is fixed to the system.

Alternatively, or in addition, the block 17 may have a rib or tongue 18, which engages in the groove 16 and improves the mutual alignment of both components 11 and 12 of the holding base 10. The rib and/or tongue 18 may be essentially parallel to the groove 16, such as for example along said non-curved extension direction of the nearby outer surface of the receiving container 110.

The attachment bar 30 may be curved at its ends and/or may be provided with loops, such as for receiving cables of probes 50. As an alternative to the embodiments shown in figures, the attachment bar 30 may also be essentially straight or non-curved. Moreover, an attachment bar may also be formed on just one side of the rail 15. The attachment bar may then be forming an angle, in a plan view, with respect to the outer surface of the outer surface of the container wall 40 facing the probe 50. Moreover, the rail 15 may also be provided with a plurality of attachment bars, which are mutually offset.

Moreover, an outer protective metal sheet may be provided on the holding base 10 for protecting the aligned probes 50 with respect to undesired external influences such as blows. A safety may be provided on the probe holder 1, for preventing the probes 50, for example, from falling down.

Figure 5A:
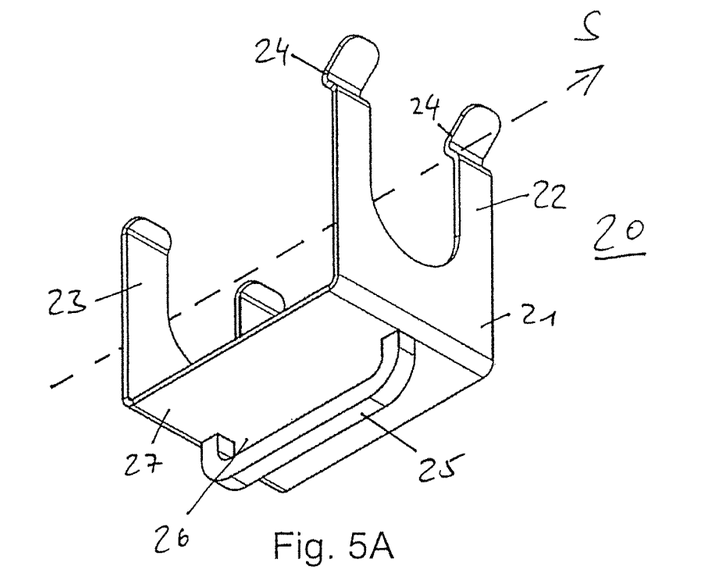
FIG. 5A shows a first perspective view of a probe positioning means of a probe holder.
Figure 5B:
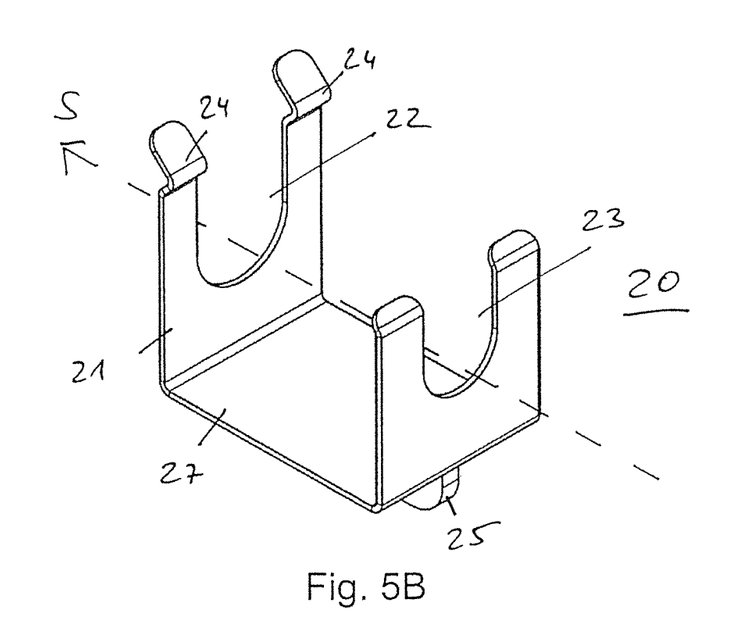
FIG. 5B shows a second perspective view of the probe positioning means of a probe holder shown in FIG. 5A.

FIGS. 5A and 5B show, in a first and second perspective view one of the probe positioning means 20 of the probe holder 1. The probe positioning means 20 has a probe housing 21, which is a region, which is configured for housing exactly one of said probes 50, for example. The probe housing 21 may be provided as a clip and/or approximately U-shaped.

The probe housing 21 has a first holding region 22 and a second holding region 23. The two holding regions 22, 23 are designed for mechanically contacting, holding and/or housing two holding points of the probe 50 which are spaced apart from one another in the direction of the probe extension direction S. Thus, the two holding regions 22, 23 may each have a recess with an inner diameter and/or an inner contour which is formed complementarily to an outer diameter and/or an outer contour of the probe 50 at each associated holding point of the probe 50. The recesses of the holding regions 22, 23 can be defined by finger ends and/or clip ends of the probe housing 21. The design of the holding regions 22, 23 determines and/or defines the position which the probe 50 occupies in the probe positioning means 20.

The probe housing 21 may also be provided with locking means 24, in particular adjacent to, proximate to and/or in at least one of the holding regions 22, 23. The locking means 24 allow the probe 50 in the probe housing 21 to latch into position. In particular, the locking means 24 can be formed on the finger ends and/or clip ends of at least one of the holding regions 22 and/or 23.

The two holding regions 22, 23 are spaced apart from each other by a central region 27. The central region 27 may be substantially flat and/or formed by sheet metal. The probe extension direction S may be approximately parallel to an extension plane of the central region 27. The length of the central region 27 in the probe extension direction S may be shorter than the length of the probe 50.

A probe 50 may be arranged with its region adjoining its attachment end 52 in the two holding regions 22, 23 such that the probe head 51 protrudes from the probe positioning means 20, in particular in the probe extension direction S.

The probes 50 may have a bellows with which the probes 50 may be introduced and/or clamped into the two holding regions 22, 23 of the probe holder 1. In particular, the probes 50 with an extended bellows, for example, may be held and supported during sealing, alignment and/or adjustment in the probe positioning means 20.

On one side of the probe housing 21, which faces away from the probe 50 in an operating position, a clamping rail 25 is formed. The clamping rail 25 may be arranged substantially parallel to the probe extension direction S and may be fixed in at least one, preferably at least two locations, to the central region 27.

Between the clamping rail 25 and the central region 27, a bar recess 26 is formed as a free space. The bar recess 26 receives the attachment bar 30. In this case, the clearance between the clamping rail 25 and the central region 27 can be substantially as large as the diameter of the attachment bar 30. In particular, the bar recess 26 may be formed slightly smaller than the diameter of the attachment bar 30, such as from about 0.1% to about 5% smaller than the diameter of the mounting bar 30. This allows the probe positioning means 20 to be clamped on the mounting bar 30, as shown, for example, in FIG. 2A.

Alternatively, the bar recess 26 may also be formed at least as large as the diameter of the bar 30, such as from about 0% to about 50% larger, preferably from about 5% larger to about 25% larger, than the diameter of the attachment bar 30. This allows the probe positioning means 20 to be moved particularly easily in the probe extension direction S, especially in case of a force caused by an expansion and/or contraction of the container wall 40. In this case, an angularly formed cross section of the attachment bar 30 can prevent or reduce tilting and/or pivoting of the probe positioning means 20 about the attachment bar 30. Such an angularly formed cross-section of the attachment bar 30 may in this case be matched to an angularly shaped cross section of the clamping rail 25, for example.

The individual probe positioning means 20 may be applied, threaded, and/or inserted onto the attachment bar 30 in a substantially horizontal direction.

The cross-section of the clamping rail 25 and/or of the attachment bar 30 may be at least partially round, angular and/or shaped as a parallelepiped. The two cross-sections can be matched with one another in order to ensure the best possible hold of the two components to each other.

The exact positioning of the probe positioning means 20 on the attachment bar 30 may be ensured by means of rings and/or clamps on the attachment bar 30, in order to prevent a slippage of the same in the probe extension direction and/or a tilting about the attachment bar 30, etc.

This kind of attachment of the probe positioning means 20 to the attachment bar 30 allows the setting of the position of the probe 50 in a first adjustment direction, i.e. the probe extension direction S. Thus, the probe positioning means 20 may be moved in and against the probe extension direction S, if the attachment bar 30 is positioned in the bar recess 26, such as by force fit and is movable along the bar recess 26.

In the example shown, the first adjustment direction, i.e. the probe extension direction S, is inclined by an inclination angle α with respect to the horizontal. In general, the first adjustment direction may be aligned by an inclination angle α to the perpendicular to the outer surfaces of the container wall 40, which face the probe 50.

The probe positioning means 20 may also be displaced in the probe extension direction of the attachment bar 30, thus allowing a second adjustment direction of the position of the probe. The probe extension direction corresponds to the extension of the attachment bar 30, which is curved, for example, and which may follow, with its curvature, the convex outer curvature of the nearby receiving container 110 of system 100, so that the attachment bar 30 is partially essentially parallel to the nearby outer surface of the receiving container 110. The second adjustment direction may thus follow a curved outer surface of system 100, in particular along the curved extension direction and/or curvature direction of the nearby outer surface.

In the example shown, the second adjustment direction is in a horizontal plane. In general, the second adjustment direction may be approximately parallel to a first extension direction of the nearby outer surface of system 100 and/or of disposable container.

Due to the two-piece holding base 10 shown in the context of FIGS. 4A and 4B, the position of probes 50 may be adjusted with respect to system 100 and/or to the disposable container, in a third adjustment direction. This third adjustment direction may be parallel to a nearby outer surface of the receiving container 110, in particular parallel to the non-curved extension direction of the nearby outer surface of the receiving container 110.

In the example, the third adjustment direction is an essentially vertical direction. In general, the third adjustment direction may be approximately parallel to the second extension direction of the nearby outer surface of system 100 and/or of disposable container. The second extension direction may be different from the first extension direction of the nearby outer surface, in particular both extension directions may be essentially perpendicular to one another. To this end, no extension direction has to follow the curvature of the receiving container, such as in the case of a receiving container with a flat wall.

FIGS. 2A and 2B show the three adjustment directions E1, E2 and E3 for a first probe 50.

Through these three different adjustment directions E1 to E3, the position of probe 50 may be set, fixed and/or aligned according to all three degrees of freedom of the space, in their respective nominal probe position.

Moreover, the probe positioning means 20 may also be tiltable about the attachment bar 30, i.e. about the second adjustment direction E2. Thus, the position of probe 50 relative to system 100 may be set in an easier and/or more precise way.

The precise nominal position of probe 50 and/or of probes 50 may be set by an operator. As an alternative, or in addition, this configuration of the probe holder 1 may entail a certain self-adjustment capability of the probe holder 1 or of the probe 50 disposed thereon, which may react, for example, to an expansion or displacement of the disposable container.

To this end, for example, the adjustment of the probe position in the first adjustment direction E1, i.e. in the probe extension direction S1, may occur automatically in case of an expansion and/or contraction of the container wall 40, to which the probe 50 is docked and/or fixed. The adjustment of the probe position in the second and/or third adjustment direction E2, E3 may be performed by an operator, for example, who positions and/or fixes the probe positioning means 20 accordingly to the holding base 10, in particular in the vertical adjustment direction E3, for example.

The adjustment of the position of the probe, in particular of the inclination angle α, may also be performed by rotating about the attachment bar 30, for example also in an automatic way, in case of an expansion and/or contraction of the container wall 40, such as in connection with a predetermined play, which may be defined by the one or more cross sections of the attachment bar 30 and/or of the clamping rail 25.

Alternatively, the inclination angle α of the probe 50 may also be adjusted or fixed by an operator.

In the context of the present invention, the terms "essentially" and/or "about" may be used such that they include a deviation of up to 5% from a numerical value following the term, a deviation of up to 5° from a direction following the term and/or from an angle following the term.

LIST OF REFERENCE NUMERALS 1 probe holder
10 holding base
11 first component fixed to the system
12 second movable component
13 positioning means
13a opening
13b screwing means
14 adjustment wheel
15 rail
15A scale
16 groove
17 block
20 probe positioning means
21 probe housing
22 first holding region
23 second holding region
24 locking means
25 clamping rail
26 bar recess
27 central region
30 attachment bar
40 container wall
41 docking device
50 probe
51 probe head
52 attachment end
100 system
110 receiving container
112 bottom window
113 cable guide
114 stirring device
115 collecting tub
118 rollers
119 fixing feet
120 system rail
130 single-leafed door
132 door window
134 door hinge
136 door knob
E1 first adjustment direction
E2 second adjustment direction
E3 third adjustment direction
L perpendicular on the vertical
S probe extension direction
S1 first probe extension direction
S2 second probe extension direction
S3 third probe extension direction
S4 fourth probe extension direction
V vertical
α inclination angle

The invention claimed is:

1. A probe holder (1) for positioning at least one probe (50) in a system (100) for biotechnological uses, the probe (50) having a body with first and second holding locations spaced apart from one another in a probe extension direction (S; S1, S2, S3, S4), the system (100) for biotechnological uses comprising a receiving container (110) that includes a rigid portion, the receiving container (110) receiving a container that has a flexible container wall (40) such that the probe (50) is at least partially engaged through the flexible container wall (40), the probe holder (1) comprising:

a holder base (10) having:
a fixed portion (11) positioned and fixed on the rigid portion of the receiving container (110) of the system (100) for biotechnological uses, and
a movable portion (12) that is adjustably movable in a base adjustment direction relative to the fixed portion (11) of the holder base (10); and at least one probe positioning means (20) having first and second holding regions (22, 23) and a central region (27) extending between the first and second holding regions (22, 23), the first and second holding regions (22, 23) releasably holding the first and second holding locations of the probe (50), the central region (27) of the at least one probe positioning means (20) being mounted to the movable portion (12) of the holder base (10) for movement of the probe (50) relative to the holder base (10) in at least one direction different from the base adjustment direction, wherein the probe positioning means (20) is for:

positioning the at least one probe (50) on the holder base (10) and relative to the rigid portion of the receiving container (110) such that a leading end of the probe (50) in the probe extension direction (S; S1, S2, S3, S4) is in an operating position where the leading end of the probe (50) is at least partially engaged through the flexible container wall (40); and adjusting a position of the probe (50) in at least the probe extension direction (S; S1, S2, S3, S4) and relative to the fixed portion (11) of the holder base (10) in response to expansion and contraction of the flexible container wall (40) while keeping the leading end of the probe in the operating position.

2. The probe holder of claim 1, wherein the probe positioning means (20) is positioned on the holder base (10) such that the position of the probe (50) in the probe extension direction (S; S1, S2, S3, S4) is automatically set in case of a force exerted in the probe extension direction (S; 51, S2, S3, S4).

3. The probe holder of claim 1, wherein the probe positioning means (20) is configured to support the entire weight of the probe (50), when the probe (50) is positioned in the probe extension direction (S; S1, S2, S3, S4).

4. The probe holder of claim 1, wherein the probe positioning means (20) is configured to house the probe (50) such that at least one probe head (51) of the probe (50) is freely directed out of the probe positioning means (50) and in the probe extension direction (S; S1, S2, S3, S4) towards the system (100) for biotechnological uses.

5. The probe holder of claim 1, wherein the probe positioning means (20) is configured to house the probe (50) with a form fit and/or a force fit.

6. The probe holder of claim 1, wherein the movable portion (12) of the holder base (10) has an attachment bar (30), onto which the probe positioning means (20) is positioned movably such that the position of the probe (50) may be variably adjusted in the probe extension direction (S; S1, S2, S3, S4).

7. The probe holder of claim 6, wherein the probe positioning means (20) is positioned on the attachment bar (30) such that the probe positioning means (20) may be displaced in the probe extension direction (S; S1, S2, S3, S4), in a bar extension direction of the attachment bar (30) and/or the probe positioning means (20) may be rotated around the attachment bar (30).

8. The probe holder of claim 6, wherein the attachment bar (30) is positioned in at least an attachment region on the probe positioning means (20) in a direction substantially perpendicular to the probe extension direction (S; 51, S2, S3, S4).

9. The probe holder of claim 6, wherein the probe positioning means (20) has an attachment means (25)

attached movably to the attachment bar (30) by a form fit and/or a force fit for enabling the probe positioning means (20) to be displaced: in the probe extension direction (S; 51, S2, S3, S4), in a bar extension direction of the attachment bar (30) and/or in rotational directions around the attachment bar (30).

10. The probe holder of claim 6, wherein the attachment bar (30) has a plurality of probe positioning means (20) positioned thereon for respectively positioning at least one probe (50) in a way that the position of the respective probe (50) is variably adjustable in its respective probe extension direction (S; S1, S2, S3, S4).

11. The probe holder of claim 6, wherein the holder base (10) has at least two attachment bars (30), on which at least one respective probe positioning means (20) is positioned for positioning a respective at least one probe (50), such that a position of the respective probe (50) is variably adjustable in its respective probe extension direction (S; 51, S2, S3, S4).

12. The probe holder of claim 1, wherein the holder base (10) is positioned on the system for biotechnological uses so that the position of the probe positioning means (20) is variably adjustable in a direction of an outer surface of the system (100) for biotechnological uses, wherein the direction of the outer surface is approximately parallel to an outer surface of the system (100) for biotechnological uses and forms an angle of at least about 45° with respect to the probe extension direction (S; S1, S2, S3, S4).

13. The probe holder of claim 12, wherein the holder base (10) has a groove (16) and a tongue (18) engaging in the groove (16), wherein the groove (16) and the tongue (18) extend approximately in parallel to each other in the direction of the outer surface.

\* \* \* \* \*